US009888977B2

(12) United States Patent
Thomas et al.

(10) Patent No.: US 9,888,977 B2
(45) Date of Patent: Feb. 13, 2018

(54) MEDICAL STERILE CONTAINER WITH SAFETY VENTILATION VALVE

(71) Applicant: Aesculap AG, Tuttlingen (DE)

(72) Inventors: Stefan Thomas, Tuttlingen (DE); Serkan Bellikli, Tuttlingen (DE); John Gray-Dreizler, Rottwell (DE); Matthias Schweizer, Tuttlingen (DE); Stefan Schuster, Villingen-Schwenningen (DE); Dieter Weisshaupt, Immendingen (DE)

(73) Assignee: Aesculap AG, Tuttlingen (DE)

( * ) Notice: Subject to any disclaimer, the term of this patent is extended or adjusted under 35 U.S.C. 154(b) by 16 days.

(21) Appl. No.: 14/951,956

(22) Filed: Nov. 25, 2015

(65) Prior Publication Data

US 2016/0151123 A1 Jun. 2, 2016

(30) Foreign Application Priority Data

Nov. 28, 2014 (DE) .................. 10 2014 117 517

(51) Int. Cl.
| | | |
|---|---|---|
| *B65D 6/40* | (2006.01) | |
| *A61B 50/33* | (2016.01) | |
| *A61B 50/30* | (2016.01) | |
| *A61B 50/00* | (2016.01) | |

(52) U.S. Cl.
CPC .............. *A61B 50/33* (2016.02); *A61B 50/30* (2016.02); *A61B 2050/006* (2016.02); *A61B 2050/0067* (2016.02); *A61B 2050/0086* (2016.02)

(58) Field of Classification Search
CPC ........ A61L 2202/122; A61L 2/26; A61L 2/07; B65D 51/16; A61B 50/00; A61B 50/30
See application file for complete search history.

(56) References Cited

U.S. PATENT DOCUMENTS

| | | | | |
|---|---|---|---|---|
| 4,349,118 A | * | 9/1982 | Sanderson | ............... A61L 2/07 220/201 |
| 4,562,047 A | | 12/1985 | Sestak | |
| 4,583,643 A | * | 4/1986 | Sanderson | ............... A61L 2/26 206/370 |
| 6,371,326 B1 | * | 4/2002 | Gabele | ...................... A61L 2/26 206/373 |
| 6,789,692 B2 | * | 9/2004 | Prezelin | ................. B65D 51/16 190/119 |
| 9,381,263 B2 | * | 7/2016 | Jacene | ...................... A61L 2/07 |
| 2009/0114646 A1 | * | 5/2009 | Whalen | .................. A45C 13/00 220/4.21 |

FOREIGN PATENT DOCUMENTS

| | | |
|---|---|---|
| DE | 1217551 | 5/1966 |
| GB | 1074275 | 7/1967 |

OTHER PUBLICATIONS

German Search Report for German Application No. 10 2014 117 517.4, dated Jul. 1, 2015, including English translation.

* cited by examiner

*Primary Examiner* — Shawn M Braden
(74) *Attorney, Agent, or Firm* — RatnerPrestia

(57) ABSTRACT

A medical sterile container includes a tray-like first container part, a lid-type second container part, a fastener and a ventilation valve to ventilate a container interior surrounded by the first container part and the second container part. The fastener is mounted on one of the container parts so as to be pivotable between a closed position, in which the container parts are locked to one another by the fastener, and an open position in which the container parts are unlocked.

13 Claims, 8 Drawing Sheets

MEDICAL STERILE CONTAINER WITH SAFETY VENTILATION VALVE

RELATED APPLICATIONS

This application is related to and claims the benefit of priority of German Application No. DE 10 2014 117 517.4, filed Nov. 28, 2014, the content of which is incorporated by reference herein in its entirety and for all purposes.

FIELD

The present invention relates generally to a medical sterile container, and more specifically to a medical sterile container with a tray-like first container part, a lid-type second container part, a fastener and with a ventilation valve to ventilate a container interior surrounded by the first and the second container part, wherein the fastener is mounted on one of the container parts so as to be pivotable between a closed position in which the container parts are locked to one another by means of the fastener and an open position in which the container parts are unlocked.

BACKGROUND

Sterile containers are used in medicine, in particular surgery, to sterilize surgical instruments, implants and the like as well as to briefly store them after sterilization and also for transportation purposes. Items to be sterilized are placed in the container interior. The container is closed by putting the container lid onto the container bottom, and then the container is placed in a sterilizer along with the items for sterilization contained inside it, where the container interior is exposed to a sterilizing gas such as steam. The gas admission is generally carried out through special filter elements. Gas exchange outside the sterilizer after sterilization is to be avoided so as to prevent recontamination. The container lid is sealed from the container bottom for this reason.

In a closed sterile container, negative pressure can be generated inside the container on closure, in particular if a compressible seal is used between the container lid and bottom. This effect can be reinforced by cooling the atmosphere in the interior of the container, in particular by means of a vacuum phase normally applied after sterilization at the end of the sterilization cycle. Disadvantageously, if a user wishes to open the container lid after sterilization without waiting, this can only be done with difficulty or is impossible due to the lower internal pressure in the container interior as compared to the environmental pressure. In this case, a delay is required until pressure equalization has occurred between the container interior and the environment, for example by leakage or via the filter elements.

A plastic sterile container for flash sterilization is also familiar from the state of the art which comprises a ventilation valve positioned in the lid of the sterile container. This is to be activated manually after sterilization by a user so as to equalize the pressure between the interior of the container and the environment. The ventilation valve is configured as a single-section silicon component, positioned in the container lid in a star-shaped recess. By means of manual activation, the silicon component can be deformed and displaced in the direction of the container interior in such a way that a bypass is created to ventilate the sterile container. Disadvantageously, the ventilation valve mounted in the container lid is freely accessible and unprotected and can be activated at any time. It is not possible to detect either a manipulation of the ventilation valve after sterilization or the associated penetration of environmental air potentially contaminated with germs. For this, care must always be taken to ensure that sterility is guaranteed in the container interior. What is more, the ventilation valve can be accidentally activated, e.g. when the container is being handled.

SUMMARY

The present invention is based on the object of providing a medical sterile container for the sterilization of medical instruments and the like which can be opened briefly or immediately after sterilization and closure in a way which is simple for the user and does not require physical effort, wherein ventilation of the sterile container occurs automatically when it is opened. Ventilation as a result of accidental activation of the valve should be very reliably prevented so as to ensure that the sterility of the sterile container and the medical equipment inside it is guaranteed until the sterile container is opened to remove the medical equipment.

The foregoing object is achieved by means of medical sterile container with a tray-like first container part, a lid-type second container part, a fastener and with a ventilation valve to ventilate a container interior surrounded by the first and second container part, where the fastener is mounted on one of the container parts so as to be pivotable between a closed position in which the container parts are locked to one another by means of the fastener and an open position in which the container parts are unlocked, where the ventilation valve is coupled with the fastener, the latter being closed in the valve's closed position and open in the valve's open position.

The first container part is preferably a container bottom comprising a container base and a container wall. The second container part is preferably a container lid to be positioned on the container wall for closing the container bottom, in particular for the purpose of pressure-tight hermetic closure. The purpose of the fastener is to allow detachable connection of the container bottom to the container lid, whereby in a closed position the fastener is held onto the container bottom and in an open position the fastener can be detached from the container bottom.

Since the ventilation valve is coupled with the fastener of the sterile container, it is automatically activated when the fastener is activated. If the fastener is closed and is in its closed position, the ventilation valve is also closed due to this coupling, thereby making ventilation impossible, in other words preventing entry of a potentially non-sterile medium from the environment of the sterile container such as air. As long as the sterile container is not opened, its sterility is ensured as is that of the medical equipment contained inside it. When the fastener is opened and moved into its open position, such as occurs when the sterile container is opened to remove the medical equipment contained inside it, the ventilation valve is opened. In other words, ventilation of the sterile container is linked to the state or activation of the fastener and the ventilation valve is open when the fastener of the sterile container is open. The result of this is that opening the fastener leads to automatic ventilation of the container interior. Advantageously, separate activation of the ventilation valve is not necessary in order to ventilate the sterile container. Due to the pressure equalization that occurs between the container interior and the environment when the fastener is opened for ventilation purposes, the sterile container according to the invention is advantageously easy for the user to open without physical effort, even immediately after closure or sterilization.

When the container lid is placed on the container bottom and the fastener is closed, the valve is activated by the latter and pressed into a closed state. This ensures that after closing the sterile container, no medium potentially contaminated with germs is able to penetrate the container interior.

The ventilation valve is preferably not accessible to a user or at least not directly accessible. In this way, faulty operation of the ventilation valve is avoided with a high degree of reliability. Activation of the ventilation valve is preferably not possible without opening the fastener of the sterile container. This ensures with a high degree of reliability that no accidental contamination can occur, except when the sterile container is opened to remove the medical equipment.

The ventilation valve is preferably located or configured in the container bottom, in particular in the wall of the container bottom. However, it can also be located or configured in the container lid. In particular, it can be concealed or covered by the fastener or by parts or partial sections of the fastener vis-à-vis the environment so that access to the ventilation valve from the outside is hindered, unless it is to be opened intentionally.

According to one preferred embodiment of the invention, the ventilation valve is pretensioned in its open position in which the container interior is ventilated. In particular, it can be pretensioned by means of a spring, e.g. a compression spring. If the ventilation valve is not activated from the outside, indicated by the fact that the fastener is closed, the ventilation valve is always in an open i.e. ventilated state. Such pretension ensures that the ventilation valve is automatically opened when the fastener is opened by a user and the container interior is ventilated.

According to a further preferred embodiment of the invention, the ventilation valve comprises a valve unit. This is preferably inserted in a clearance hole in the bottom or lid of the container. The valve unit seals the clearance hole in a suitable manner when the ventilation valve is closed. This can preferably be achieved by fitting the valve unit on the wall area of the container bottom or lid that surrounds the clearance hole.

Preferably the valve unit is essentially mushroom-shaped in configuration, with a valve unit shaft and a valve unit head. The valve unit shaft can comprise at least one spring-biased latch element, preferably several spring-biased latch elements, as an end stop and position limiter for the valve unit in the open valve position. Preferably, the valve unit is essentially made of plastic. It can comprise a silicon seal which is close-fitting so as to seal the container bottom or lid in the closed position. In particular, the silicon seal can be configured as a single part combined with the valve unit by means of 2K technology. Preferably it is located on a lower side of the valve shaft head facing towards the container bottom or lid. Advantageously, such a valve unit is simple and low-cost to produce and easy to install. For this purpose it is inserted in the clearance whole in the bottom or lid of the container where the latch element or elements deflect due to their elastic properties when passing through the clearance hole and spring back into their original position when they have passed through the clearance whole. In this original position, the latch element forms an end stop which is in force when the open position of the ventilation valve on the bottom or lid of the container is reached so that it is not possible to detach the valve unit through the clearance whole.

According to a preferred embodiment of the invention, the valve unit, in particular the valve unit shaft, should be hollow at least in sections and comprise a blind hole. The blind hole preferably holds the spring which pretensions the valve unit in the open position. The spring is preferably a compression spring. It can be mounted firstly at the closed end of the blind hole and secondly in particular on a functional unit which is positioned up against a wall of the container bottom or lid in the container interior. Alternatively, the compression spring can be mounted on a container tray positioned in the container interior. The spring can also be mounted directly on the container wall.

In another preferred embodiment, the fastener of the sterile container comprises a fastener cap. This is preferably positioned on the lid of the container but can also be positioned on the container bottom. In the closed position of the fastener, the fastener cap engages behind a latch structure on the container bottom (or lid) in such a way that the container lid is kept firmly on the container bottom. It is particularly advantageous if the ventilation valve is positioned under the fastener, in particular under the cap of the fastener. The valve is then inaccessible to a user and not subject to manipulation, which ensures sterility as long as the sterile container has not yet been opened. In addition, the ventilation valve is concealed behind the fastener/fastener cap when the latter is closed and is not visible, thereby providing additional protection against manipulation.

It is especially advantageous if the fastener cap, when in its closed position, engages with the valve unit, in particular the valve unit head, and presses the valve unit into the closed valve position. In this way, direct activation of the ventilation valve is dependent on the functional position of the fastener or fastener cap.

In a preferred embodiment, the fastener can comprise a lock element. This can lock the fastener and in particular the fastener cap in the closed position. Particularly advantageously, opening of the fastener and therefore ventilation of the container interior is only possible by first deliberately releasing the lock element and then opening the fastener or fastener cap. This further reduces the probability of accidental ventilation of the container interior with potential contamination. In this preferred embodiment, it is especially advantageous if, when the fastener cap is in its closed position, the lock element engages with the valve unit, in particular the valve unit head, and presses the valve unit into the closed valve position. Here the ventilation valve is activated directly by the lock element. Provision can also be made for the lock element to engage with the valve unit, in particular the valve unit head, and to press the latter into the closed valve position when the lock element is in the position in which it locks the fastener cap.

It is also advantageous for the ventilation valve to be able to be automatically closed when the sterile container is closed with the container lid so that no separate manipulation of the ventilation valve is necessary after closing the container, thereby ensuring leak-tightness and therefore sterility. When the container lid is placed on the container bottom and the fastener closed, the valve is automatically or forcibly activated by the fastener or fastener cap and moved into the closed position against its pretension, thereby sealing the clearance opening. When the fastener latches into the relevant mating latch, the ventilation valve is closed. When the fastener is opened again, the ventilation valve automatically moves into the open position due to its pretension.

By linking the ventilation function to the function of the fastener, a safety ventilation valve is created which only ventilates when the sterile container is deliberately opened. Unintentional opening or activation of the valve is ruled out and the sterility of the container is ensured until the lid is opened.

According to another aspect, the ventilation valve is pretensioned in a closed valve position, in particular by means of a spring, and is pressed into an open valve position by means of a tilt lever mechanism which is pivot-mounted and pretensioned on the sterile container, in particular on the container bottom, and in contact with the ventilation valve, whereby the fastener blocks the tilt lever mechanism in its closed position and releases it in its open position.

According to this aspect, the normally closed ventilation valve is forcibly or actively opened when the fastener is opened by means of a lever mechanism which operatively interacts with the fastener. With this solution it is possible to use a valve which is available on the sterile container anyway, for example a valve by which gas or steam is applied to the container interior during the sterilization process. This valve then performs two functions, firstly that of an automatically opening negative or positive pressure valve and secondly that of a ventilation valve which is to be forcibly opened when the fastener is opened.

According to this aspect, the torque applied by the pretension force of the tilt lever mechanism to the tilt lever can be greater than the torque applied by the pretension force of the ventilation valve to the tilt lever. In this way, firstly the ventilation valve is automatically closed when the fastener is closed and only opens under certain pressure conditions, and secondly the ventilation valve is automatically opened via the tilt lever mechanism against its pretension when the fastener is opened.

According to one aspect, the ventilation valve pretensioned in its closed valve position can be moved into its open valve position when the relevant negative or positive pressure applies, if the fastener is in its closed position. This means that the ventilation valve is not limited in its actual function as a negative or positive pressure valve. The tilt lever mechanism operatively interacts with the ventilation valve in such a way that it can only activate or open the later in one direction.

What is more, the fastener can comprise a lock element which locks the fastener, in particular the fastener cap, in its closed position. When the fastener cap is in the closed position, the lock element can be connected to a lever end of the tilt lever mechanism and thereby cancel out a pretension force of the other lever end acting on the ventilation valve. In the dosed position, the fastener, or to be more precise the lock element, thereby prevents the tilt lever mechanism from activating or opening the ventilation valve. The tilt lever mechanism is moved by the fastener or its lock element into a position in which it does not exert any force on the ventilation valve, so that the ventilation valve is closed due to its own pretension. When the fastener is removed along with the lock element, the tilt lever mechanism presses the ventilation valve into the open valve position due to its pretension.

According to one aspect, the ventilation valve can be fitted with one or more filter elements and serve the purpose of gas admission during the sterilization process. In this way, a valve filter element provided for the sterilization process can serve as a ventilation valve through forcible activation.

BRIEF DESCRIPTION OF THE DRAWING FIGURES

Features and benefits of the present invention are illustrated by the following exemplary description of the invention and a particularly preferred though not limiting embodiment based on figures. The figures are diagrammatic in nature only and serve solely to explain the non-limiting embodiment of the invention. The figures are as follows:

FIG. 1 diagrammatically shows an area of a fastener of a sterile container according to a first preferred embodiment in a perspective cross-section view;

DETAILED DESCRIPTION

Figure 1:
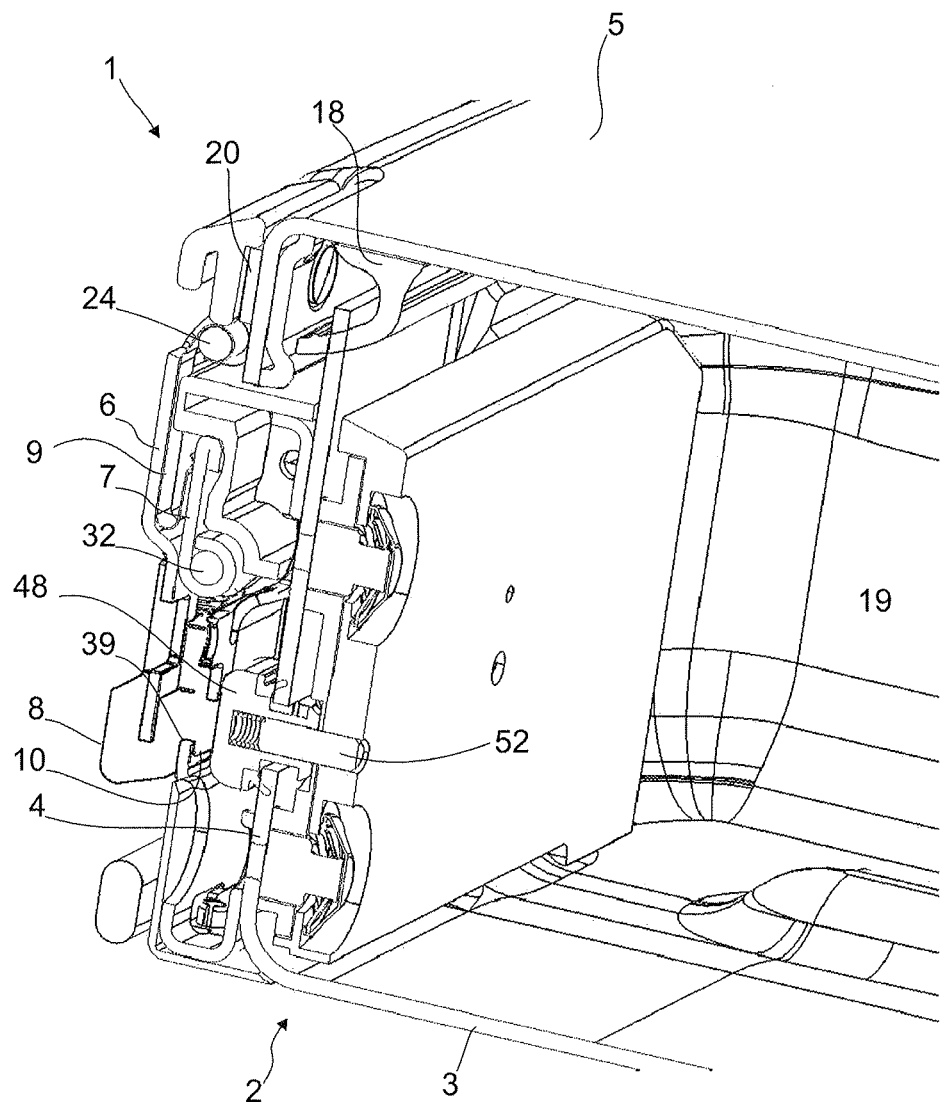
Figure 2:
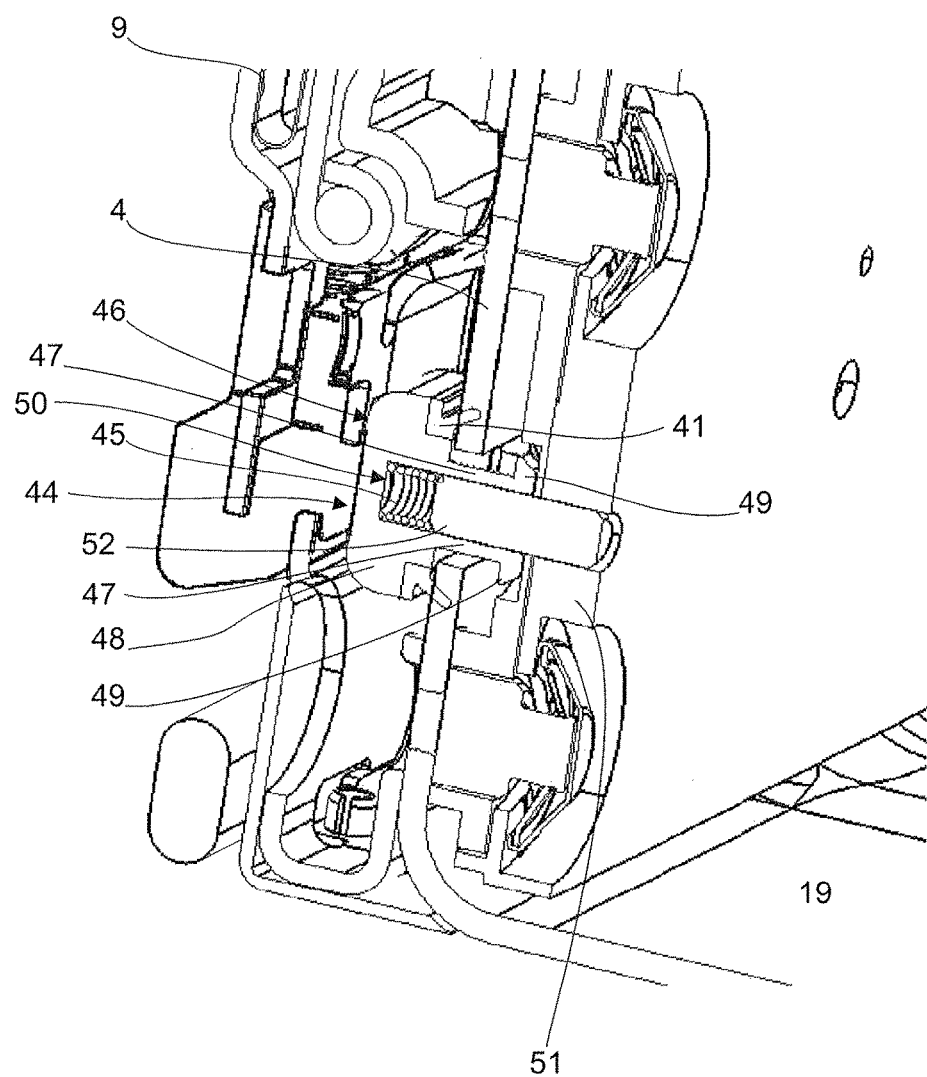
FIG. 2 shows an enlarged section of FIG. 1.

FIGS. 1 and 2 show a section of a container bottom 2 of the sterile container 1 with a fastener in closed position. The container bottom 2 comprises a container base 3 and a container wall 4. A container lid 4 is placed or is to be placed on the container wall 4. The container lid 5 is sealed from the container wall 4 by means of a seal 18 in such a way that when the sterile container 1 is closed, its interior 19 is hermetically sealed from the environment, with the exception of any filters and filter openings which may be present, though these are not shown in the figures.

The container lid 5 comprises a lid tongue 20, in particular attached by means of rivets or screws. The lid tongue 20 is a moulded sheet metal part and is shown in perspective in FIG. 1.

A fastener cap 6 is pivot-mounted about a fastener axis 24 on the lid tongue 20, positioned on the lid tongue 20 and therefore on the lid 5. The fastener cap 6 is likewise configured as a moulded sheet metal part.

A closure tongue 7 is pivot-mounted about a closure tongue axis 32, positioned on the fastener cap 6. The closure tongue 7 is configured as a moulded sheet metal part. The fastener cap 6 and the closure tongue 7 go together with the pivot axes 24 and 32 to form a toggle lever mechanism.

The fastener also comprises the lock element 8. In the embodiment shown, this is configured as a plastic injection-moulded part. The lock element 8 can be moved in relation to the fastener cap 6 between a lock position and a release position, in the longitudinal direction of the fastener. In the lock position, the lock element 8 is able to lock the fastener vis-à-vis the sterile container 1 in the latter's closed position. In the release position, the lock element 8 is able to release the fastener vis-à-vis the sterile container 1 out of the latter's closed position. For the purpose of locking the fastener with the sterile container 1, the lock element 8 comprises a catch 10 which can interlock with a locking edge 39 of the container bottom 2.

The fastener cap 6 and the closure tongue 7 are pretensioned against each other by means of a fastener spring 9. The container wall 4 comprises a clearance hole which opens to the container interior 19 in one direction and to the surrounding environment of the container 1 in the other direction. A valve unit 46 of a ventilation valve 44 is located in the clearance hole. This valve unit comprises a valve unit shaft 47 and a valve unit head 48. The valve unit shaft 48 is slotted, in other words it has several arms of which two can be seen in the figure. At the end of the valve unit shaft 47 which is opposite the valve unit head 48, each arm is provided with a latch element 49 which fits against the side of the container wall 4 facing the container interior 19 in the open position of the ventilation valve 44 and forms an end stop which limits the open position. The valve unit 46 guided axially on a valve pin 52.

The valve unit head 48 comprises a ring-shaped silicon seal 41 on its side facing the container wall 4. In FIGS. 1 and 2, the ventilation valve 44 is shown in its closed position in which the valve unit head 48 fits against the side of the container wall 4 facing away from the container interior 19 as a result of interaction with the catch 10, sealing the container wall 4 from the clearance hole in the container wall 4 by means of the silicon seal 41.

The valve unit shaft 47 is partially hollow in configuration with a blind hole 50. Inside this there is a compression spring 45 which is mounted firstly on the valve unit head 48 and secondly on the valve pin 52 positioned on the container wall 4. It can alternatively be mounted on a functional unit 51 located in the container interior 19. In the closed position of the ventilation valve 44 shown in the figure, the compression spring 45 is compressed and tensions the valve unit outwards into the open position of the ventilation valve 44.

Figure 3:
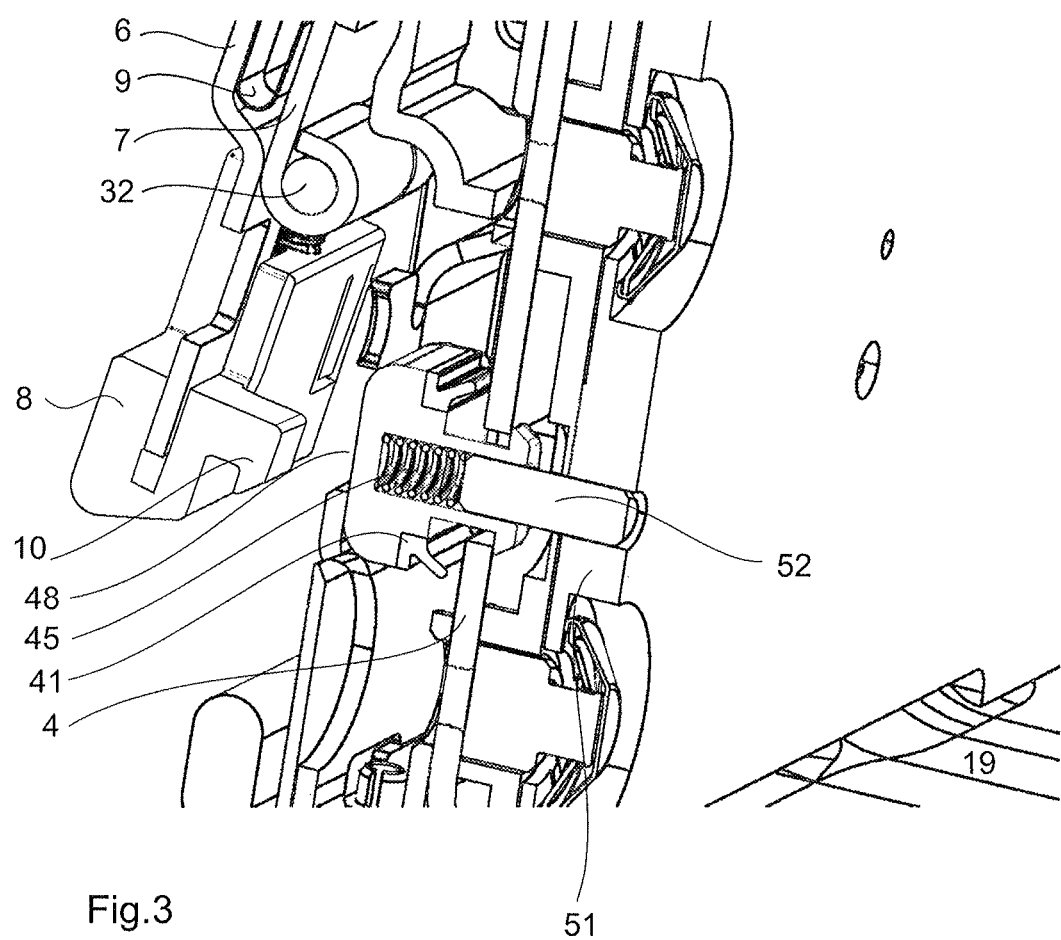
FIG. 3 shows the same section as FIG. 2 with the fastener slightly opened.

Furthermore, the lock element 8 or its catch 10 engages with the valve unit head 48. The lock element 8 or the catch 10 presses the valve unit 46 against the pretension of the spring 9 into the closed position of the ventilation valve 44 shown in FIGS. 1 and 2. When the sterile container 1 is opened by a user, for example in order to remove sterilized medical instruments from the container interior 19, the lock element 8 first has to be released from the locked position shown in the figure by being shifted upwards (in FIG. 1 upwards and slightly to the right). In doing so, the catch 10 or the lock element 8 is detached from the locking edge 39. The fastener cap 6 can then be pivoted about the axis 24. Here the closure tongue 7 is detached from the container bottom 2 and the container lid 5 is released. When the fastener cap 6 is pivoted, the lock element 8 or catch 10 is detached from the valve unit head 48 and releases the latter. Due to the pretension of the spring 45, it is moved from the closed position shown in FIGS. 1 and 2 into the open position in which the valve unit head 48 is no longer in a close-fitting sealing position up against the container wall 4. FIG. 3 shows the fastener in such an open position. The silicon seal 41 is no longer up against the container wall 4 and a flow connection is formed from outside through the opening in the container wall 4 past the silicon seal 41, the valve unit shaft arms 48 and the latch elements 49 into the container interior 19. Opening the fastener 43 therefore directly causes ventilation of the container interior 19 via the ventilation valve 44.

FIGS. 4 to 9 show another preferred embodiment. While in the first preferred embodiment the ventilation valve 44 is solely intended for ventilation of the container interior 19 when the fastener 43 is opened, in the second preferred embodiment one of the valves already provided for the sterilization process is used for this purpose.

Figure 4:
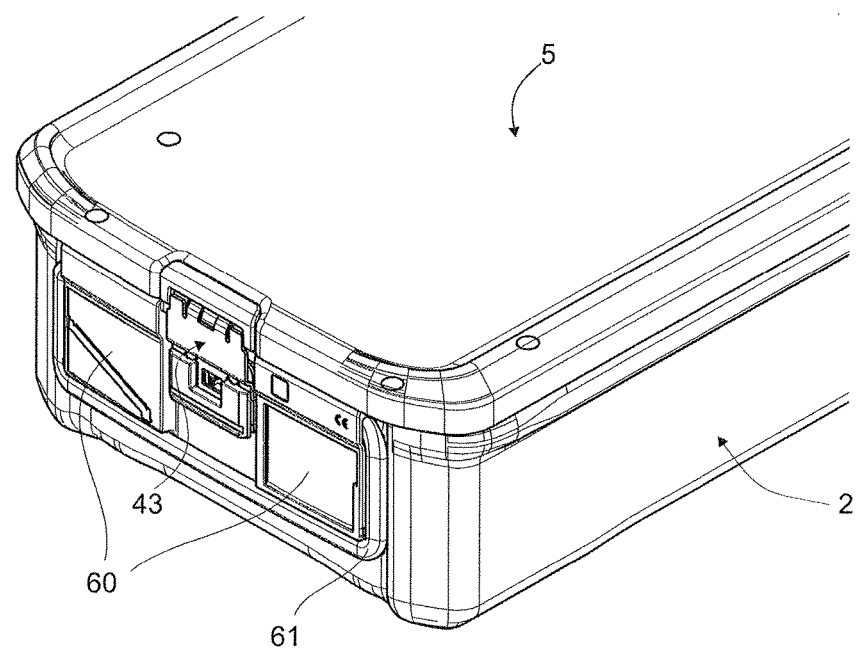
FIG. 4 shows a perspective partial view of a sterile container with a fastener according to a second preferred embodiment.

FIG. 4 shows a perspective partial view of a sterile container 1 according to the second preferred embodiment. The sterile container 1 comprises a container bottom 2 with a container top or container lid 5 which is closed by means of a fastener 43. In addition to the fastener 43, the sterile container 1, or more precisely the container bottom 2, exhibits on its front or short side to the left and right of the fastener 43 a label holder 60 in each case and a handle 61 enclosing the label holder 60 which can be pivoted outwards and which is provided for the purpose of lifting and carrying the sterile container 1.

Figure 5:
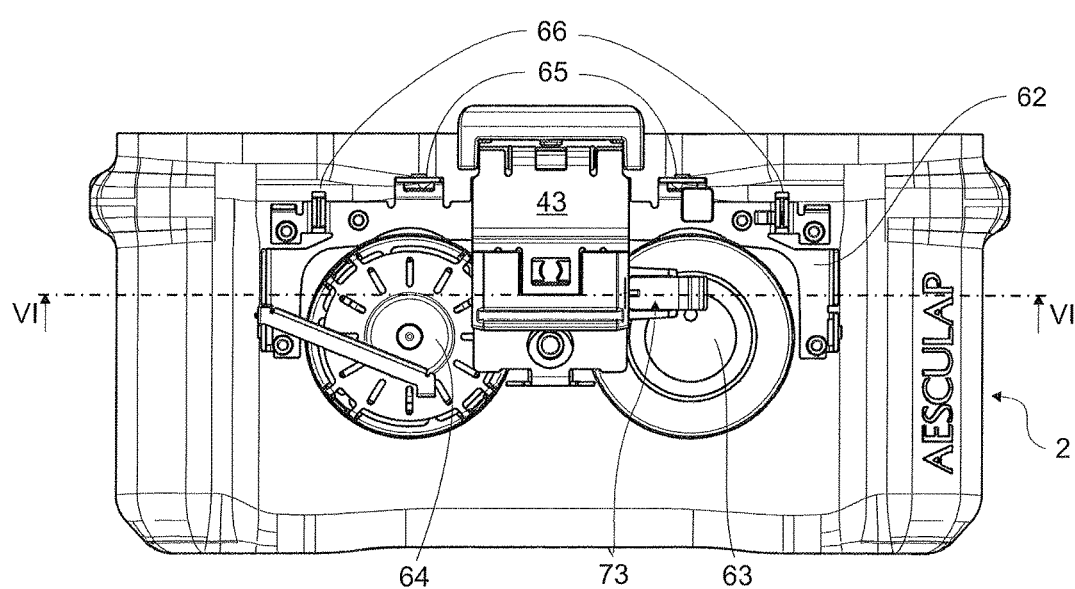
FIG. 5 shows a front view of the fastener according to the second preferred embodiment on a container bottom.

FIG. 5 shows a front view only of the container bottom 2 (i.e. without the container lid 5), but with the entire fastener 43 and with the label holders 60 and handle 61 removed. After removal of the label holder 60 and the handle 61, an attachment frame 62 and two valve filter elements 63 and 64 are revealed. The attachment frame 62 is fixed to the outside wall of the container bottom 2 by rivets or otherwise and comprises firstly retaining sections 65 for the label holders 60 and secondly retaining sections 66 for the respective ends of the handle 61. The two valve filter elements 63 and 64 serve the purpose of gas admission to the container interior 19 and of gas recovery from the container interior 19 in the case of steam sterilization.

Figure 6:
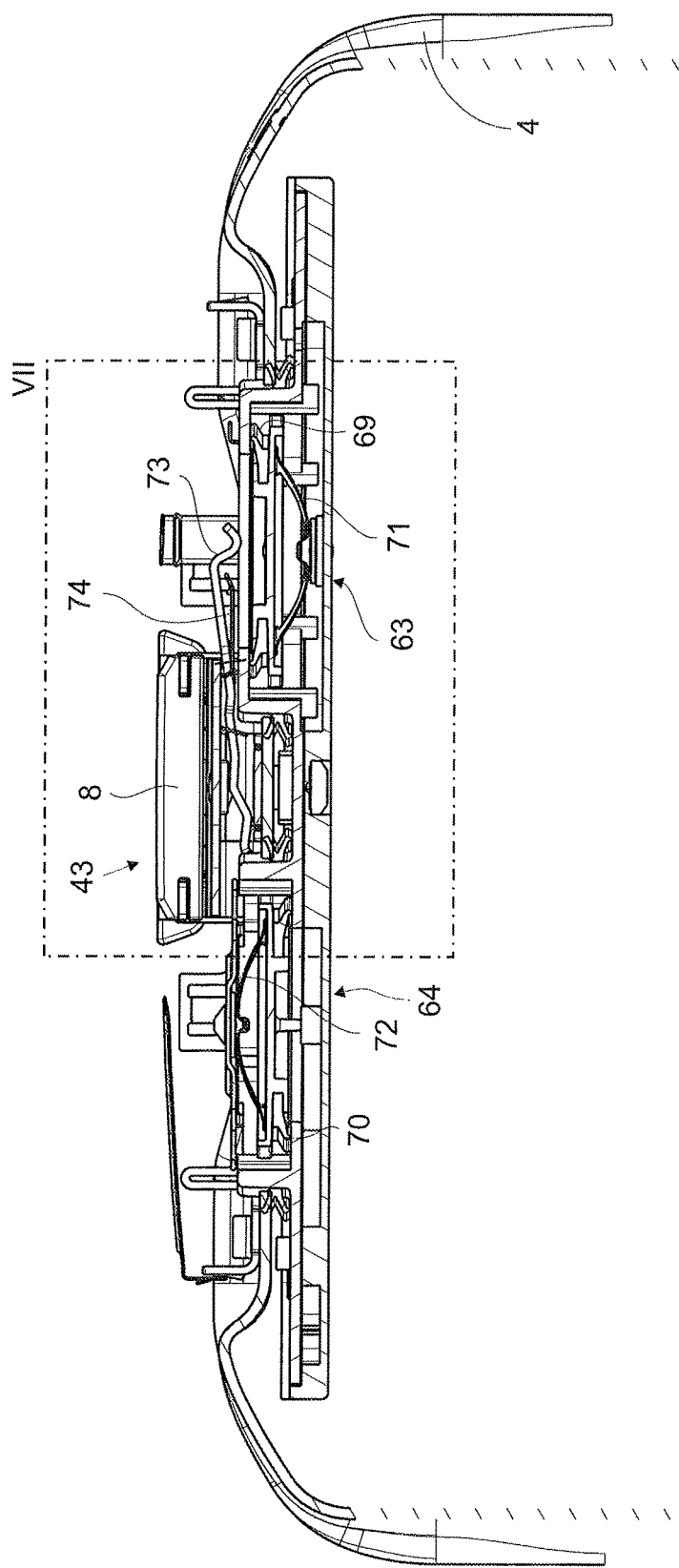
FIG. 6 shows a VI-VI cross-section view depicted in FIG. 5.

FIG. 6 shows the VI-VI cross-section view depicted in FIG. 5. The two valve filter elements 63 and 64 are each sealed with a spring-mounted seal or valve element 69, 70. The valve filter element 63 is a valve or negative pressure valve that opens inwardly against the spring pretension of a valve spring 71 and valve filter element 64 is a valve or positive pressure valve that opens outwardly against the spring pretension of a valve spring 72.

The seal 69 of the valve filter element 63 opens on gas admission from a certain pressure so as to allow the gas required for sterilization purposes, e.g. steam, to flow into the sterile container 1. The gas contained in the sterile container 1 prior to sterilization flows out or is extracted via the valve filter element 63 and 64.

The valve filter element 63 or its valve seal 69 serves as a ventilation valve in order to achieve pressure equalization before the container lid 5 is opened. This forms a force fit with the fastener 43 and in particular with the lock element 8 or its catch 10 via a lever or toggle mechanism 73 and is forced open or opens automatically when the fastener 43 is open or when the lock element 8 is unlocked.

Figure 7A:
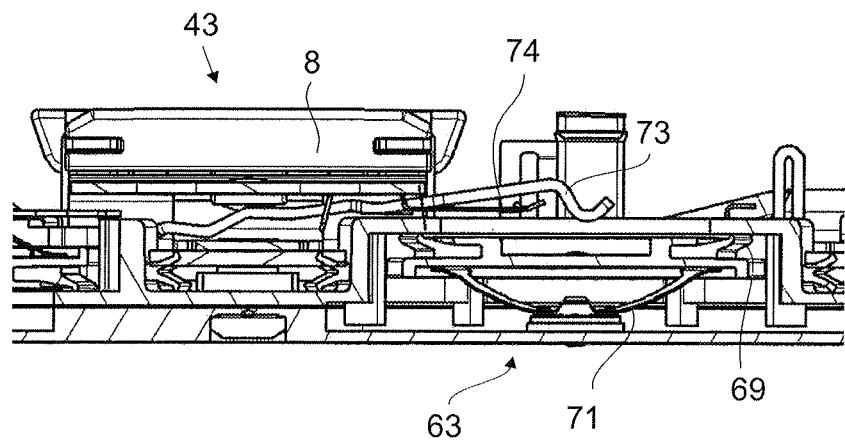
FIGS. 7A and 7B show the detailed view of FIG. 6 in various positions of the fastener according to the second preferred embodiment.
Figure 7B:
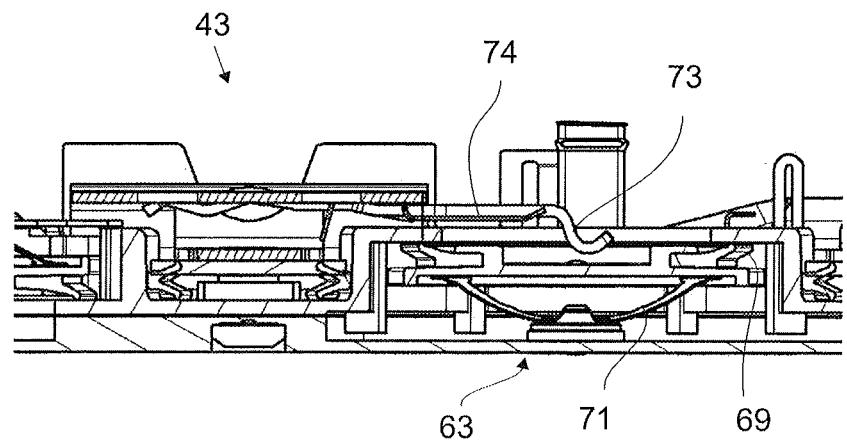

This automatic opening of the valve seal 69 for the purpose of pressure equalization when opening the fastener 43 occurs via the lever or toggle mechanism 73, which is coupled with the fastener 43 on one side of the lever arm (fastener side) and on the other side of the lever arm (valve side) moves the valve filter element 63 or its valve seal 69 out of the closed position (cf. FIG. 7A) into the open position (cf. FIG. 7B).

The lever mechanism 73 is pivot-mounted on the attachment frame 62 and is pretensioned by means of a spring 74, in particular a compression or leaf spring, towards the valve filter element 63 or in the direction of the latter's opening. When the fastener 43 is closed or when the lock element 8 is locked or when the fastener cap 6 is in its closed position, the lever mechanism 73 is pivoted away from the valve filter element 63 against the spring pretension of the spring 74 via the fastener 43, or more precisely via the lock element 8. The lever mechanism 73 presses on the fastener side against the lock element 8 from the inside. In other words, the fastener 43 or the lock element 8 blocks the lever mechanism 73.

When the lock element 8 is unlocked and the fastener cap 6 is pivoted away to the outside, this releases the lever mechanism 73 and the latter pivots towards the valve filter element 63 due to the spring pretension of the spring 74 and presses the valve filter element 63 open against the pretension force of the valve spring 71.

Figure 8A:
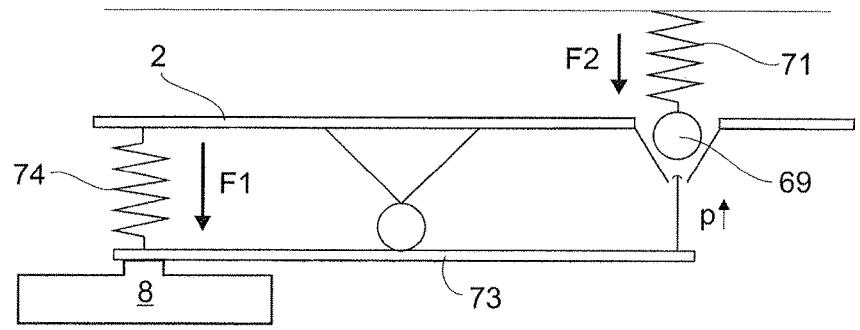
FIGS. 8A, 8B and 8C show diagrammatic depictions of the operating principle of the fastener according to the second preferred embodiment.
Figure 8B:
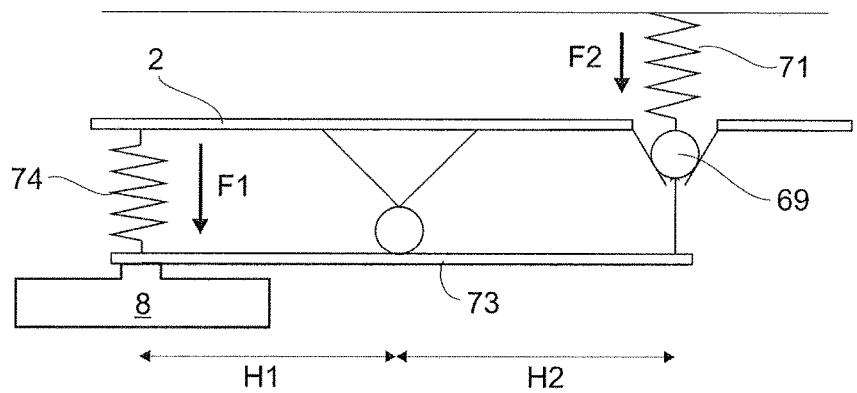
Figure 8C:
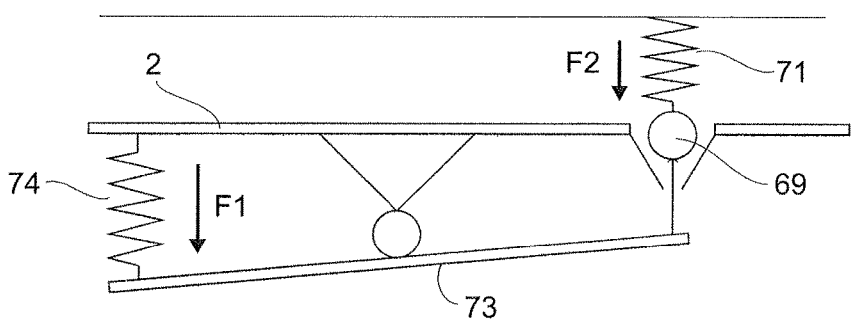

The operating principle is shown diagrammatically in FIG. 8A to 8C.

In FIG. 8A, the sterile container 1 is closed. The fastener cap 6 is in the closed position and the lock element 8 is in the locked position. The lever mechanism 73 is held by the fastener cap 6 or pressed inwards towards the container wall 4, thereby preventing the pretensioned lever mechanism 73 from activating and opening the valve filter element 63. Even if the valve filter element 63 is not opened by the lever mechanism 73, it opens on its own when the appropriate pressure is applied against the spring pretension F2 of the valve spring 71, e.g. in the case of gas admission for the purpose of steam sterilization. This is possible since the lever mechanism 73 is not connected to the valve filter element 63 and only activates or can only activate the valve filter element 63 by contact in one direction.

FIG. 8B shows the state after the sterilization process. The valve filter element 63 is closed by the spring pretension F2 of the valve spring 71. Such pretension ensures that the ventilation valve is not automatically opened until the fastener 43 is opened by a user and the container interior 19 is ventilated. The lever mechanism 73 is held in place by the closed fastener cap 6.

When the fastener 43 is opened, as shown in FIG. 8C, and the fastener cap 6 and lock element 8 removed, the lever mechanism 73 is pivoted towards the valve filter element 63 by the spring force of the spring 74 and the lever mechanism 73 opens the valve seal 69 against the spring pretension F2 of the valve spring 71. The leverage forces are selected in such a way that the leverage force on the fastener side from pretension force F1 combined with the lever arm M1 is greater than the leverage force from pretension force F2 of valve spring 71 and lever arm H2 on the valve side, and the lever mechanism 73 automatically tips into the ventilation position when the fastener 43 is opened, pressing the valve seal 69 inwards or opening it.

When the fastener 43 is locked, the lever mechanism 73 is once again moved into the resting positing against the pretension of the spring 74 so that the seal 69 once again closes due to the spring force F2 of the valve spring 71.

Figure 9A:
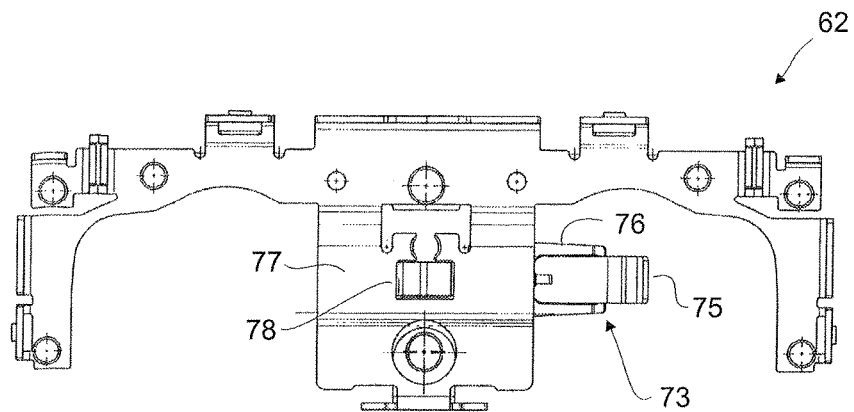
FIGS. 9A, 9B and 9C show views of an attachment frame and a tilt lever mechanism of the fastener according to the second preferred embodiment.
Figure 9B:
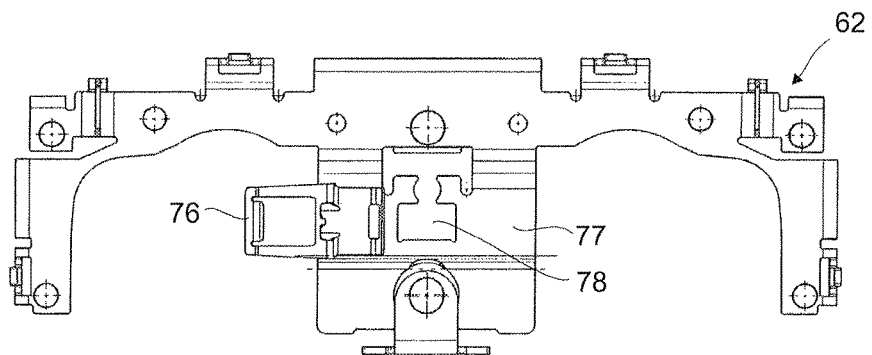
Figure 9C:
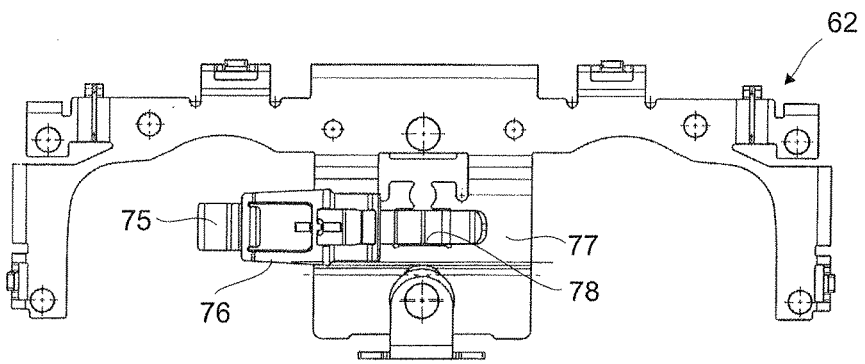

FIGS. 9A to 9C only show the attachment frame 62 and the connection of the lever mechanism 73 to it.

FIG. 9A shows a front view of the attachment frame 62 and the lever mechanism 73 attached to it, FIG. 9B shows a rear view of the attachment frame 62 without the lever mechanism 73 and FIG. 9C shows a rear view of the attachment frame 62 complete with lever mechanism 73. The lever mechanism 73 comprises a tilt lever 75 which is guided in a lever receptacle 76, pivot-mounted in the latter and pretensioned with the pretension spring 74 (not shown) in one direction. The lever receptacle 76 is attached, e.g. welded, to the back of a central section 77 of the attachment frame 62 positioned between the two valve filter elements 63, 64 and inside the fastener cap 6, i.e. between the attachment frame 62 and the container wall 4.

In the section 77, the attachment frame 62 comprises an opening 78 through which the catch 10 of the lock element 8 can engage and positively connect behind it in the locked position. The part of the lever 75 on the fastener side reaches behind the section 77, i.e. between the attachment frame 62 and the container wall 4, and is pressed against the back of the section 77 by the spring force of the pretension spring 74. The part of the lever 75 on the fastener side is shaped so that it reaches into or through the opening 78.

If the fastener 43 is now closed, the catch 10 of the lock element 8 reaches through the opening 78 from the outside and presses the part of the lever 75 on the fastener side towards the container wall 4, whereby the end of the lever 75 on the valve side is pivoted away by the valve filter element 63 and the valve filter element 63 is closed.

When the fastener cap 6 along with the lock element 8 and the catch 10 are pivoted outwards to open the fastener 43, the part of the lever 75 on the fastener side can pivot outwards again or the end of the lever 75 on the valve side can once again pivot inwards so as to open the valve filter element or the ventilation valve 63.

Various preferred embodiments of a medical sterile container have been described in which a ventilation valve is coupled with the fastener in each case, either indirectly or directly, in such a way that when the fastener is opened, the ventilation valve is also opened.

The invention claimed is:

1. A medical sterile container with a first container part, a second container part, a fastener and a ventilation valve to ventilate a container interior surrounded by the first container part and the second container part,
    the fastener being mounted on one of the container parts so as to be pivotable between a closed position in which the container parts are locked to one another by the fastener, and an open position in which the container parts are unlocked,
    the ventilation valve being coupled with the fastener, being closed in the closed position of the fastener and open in the open position of the fastener,
    wherein the ventilation valve is pretensioned in an open valve position by a spring arranged within the ventilation valve, and
    wherein the ventilation valve is pressed into a closed valve position by the fastener in the closed position.

2. The medical sterile container according to claim 1, wherein the ventilation valve comprises a valve unit being at least partially hollow in configuration with a blind hole in which the spring is mounted.

3. The medical sterile container according to claim 1, wherein the fastener comprises a lock element which locks a fastener cap in a closed fastener cap position, and wherein, when the fastener cap is in the closed fastener cap position, the lock element engages with a valve unit of the ventilation valve, and forces the ventilation valve into the closed valve position.

4. The medical sterile container according to claim 1, wherein the ventilation valve comprises a valve unit, and the valve unit is inserted in a clearance hole of the first container part or the second container part and which seals the clearance hole when the ventilation valve is in the closed valve position.

5. The medical sterile container according to claim 4, wherein the valve unit is mushroom-shaped in configuration with a valve unit shaft and a valve unit head, wherein the valve unit shaft comprises a spring-biased latch element which forms an end stop and position limiter for the valve unit in the open valve position.

6. The medical sterile container according to claim 5, wherein the valve unit shaft is at least partially hollow in configuration with a blind hole in which the spring is mounted.

7. The medical sterile container according to claim 3, wherein the ventilation valve comprises the valve unit which is inserted in a clearance hole of the first container part or the second container part and which seals the clearance hole when the ventilation valve is in the closed valve position.

8. The medical sterile container according to claim 7, wherein the valve unit is mushroom-shaped in configuration with a valve unit shaft and a valve unit head, wherein the valve unit shaft comprises a spring-biased latch element which forms an end stop and position limiter for the valve unit in the open valve position.

9. The medical sterile container according to claim 8, wherein the valve unit shaft is at least partially hollow in configuration with a blind hole in which the spring is mounted.

10. The medical sterile container according to claim 4, wherein the valve unit is at least partially hollow in configuration with a blind hole in which the spring is mounted.

11. The medical sterile container according to claim 7, wherein the valve unit is at least partially hollow in configuration with a blind hole in which the spring is mounted.

12. A medical sterile container with a first container part, a second container part, a fastener and a ventilation valve to ventilate a container interior surrounded by the first container part and the second container part, the fastener being mounted on one of the container parts so as to be pivotable between a closed position in which the container parts are locked to one another by the fastener, and an open position in which the container parts are unlocked, the ventilation valve being coupled with the fastener, being closed in the closed position of the fastener and open in the open position of the fastener, wherein the ventilation valve comprises a valve unit, and the valve unit is inserted in a clearance hole of the first container part or the second container part, the valve unit sealing the clearance hole when the ventilation valve is closed, wherein the valve unit is mushroom-shaped in configuration with a valve unit shaft and a valve unit head, wherein the valve unit shaft comprises a spring-biased latch element which forms an end stop and position limiter for the valve unit when the valve unit is open.

13. A medical sterile container with a first container part, a second container part, a fastener and with a ventilation valve to ventilate a container interior surrounded by the first container part and the second container part, the fastener being mounted on one of the container parts so as to be pivotable between a closed position in which the container parts are locked to one another by the fastener, and an open position in which the container parts are unlocked, the ventilation valve being coupled with the fastener, being closed in the closed position of the fastener and open in the open position of the fastener, wherein the ventilation valve comprises a valve unit, and the valve unit is inserted in a clearance hole of the first container part or the second container part, the valve unit sealing the clearance hole when the ventilation valve is closed, wherein the valve unit is at least partially hollow in configuration with a blind hole in which a spring is mounted.

* * * * *